United States Patent
Fernandez et al.

(10) Patent No.: US 9,738,590 B1
(45) Date of Patent: Aug. 22, 2017

(54) METHOD OF MELT POLYMERIZING POLYCARBONATE AND THE POLYCARBONATE MADE THEREFROM

(71) Applicant: SABIC Global Technologies B.V., Bergen op Zoom (NL)

(72) Inventors: Ignacio Vic Fernandez, Murica (ES); Paulus Johannes Maria Eijsbouts, Nieuwkuijk (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/502,539

(22) PCT Filed: Sep. 4, 2015

(86) PCT No.: PCT/IB2015/056770
§ 371 (c)(1),
(2) Date: Feb. 8, 2017

(87) PCT Pub. No.: WO2016/035051
PCT Pub. Date: Mar. 10, 2016

(30) Foreign Application Priority Data

Sep. 5, 2014 (EP) .................................... 14382331

(51) Int. Cl.
| C08G 64/00 | (2006.01) |
| C07C 68/06 | (2006.01) |
| C08G 64/30 | (2006.01) |
| C08G 64/06 | (2006.01) |
| C08G 63/02 | (2006.01) |

(52) U.S. Cl.
CPC .............. *C07C 68/06* (2013.01); *C08G 64/06* (2013.01); *C08G 64/307* (2013.01)

(58) Field of Classification Search
CPC ....................................................... C07C 68/06
USPC .................................................. 528/196, 198
See application file for complete search history.

(56) References Cited

U.S. PATENT DOCUMENTS

| 6,277,945 B1 * | 8/2001 | Hachiya .................. C07C 37/20 528/196 |
| 7,067,610 B2 | 6/2006 | Vaporciyan |
| 2014/0206833 A1 | 7/2014 | Fernandez et al. |

OTHER PUBLICATIONS

International Search Report for International Application No. PCT/IB2015/056770; International Filing Date Sep. 4, 2015; Date of Mailing Mar. 14, 2016; 7 pages.
Written Opinion of the International Search Report for International Application No. PCT/IB2015/056770; International Date Sep. 4, 2015; Date of Mailing Mar. 14, 2016; 7 pages.

* cited by examiner

*Primary Examiner* — Terressa Boykin
(74) *Attorney, Agent, or Firm* — Cantor Colburn LLP (57) ABSTRACT

In an embodiment, a method for producing an aryl alkyl carbonate can comprise: reacting methanol with a dicarbonate in the presence of a catalyst to form a mixture comprising an aryl alkyl carbonate and a hydroxy compound, where methanol is in an acetone monomer mixture comprising acetone and at least one of diaryl carbonate and dihydroxy compound separating the aryl alkyl carbonate from the mixture.

20 Claims, 3 Drawing Sheets

METHOD OF MELT POLYMERIZING POLYCARBONATE AND THE POLYCARBONATE MADE THEREFROM

CROSS REFERENCE TO RELATED APPLICATIONS

This application is a National Stage application of PCT/IB2015/056770, filed Sep. 4, 2015, which claims the benefit of EP Application No. 14382331.8, filed Sep. 5, 2014, both of which are incorporated by reference in their entirety herein.

TECHNICAL FIELD

The present disclosure relates to aryl alkyl carbonates and methods for making and for using the same.

BACKGROUND

Polycarbonate is a widely used raw material in many different manufacturing sectors. Due to the hardness and transparency of the material, it can be applied in applications as diverse as automotive windows and optical lenses. It is believed that the demand for polycarbonate will increase significantly in the coming years, requiring improvement in the production of polycarbonate, particularly in terms of efficiency and environmental impact.

Polycarbonate can be polymerized via the reaction of a dihydroxy compound, such as a bisphenol, and a carbonate source, such as a diaryl carbonate. For the industrial production of polycarbonate, where the monomers are not produced onsite, large amounts of these monomers need to be transported to the production facility. The use of a diaryl carbonate has the advantage that it is reactive enough to form polymeric polycarbonate. Furthermore, the reaction of diphenyl carbonate to form polycarbonate phenol is liberated. This phenol can be recycled and used in the production of, for example, bisphenol A or diphenyl carbonate that can be used as main raw material in the polymerization.

Due to the increasing demands on polycarbonate production, the process for production of polycarbonate leaves ample room for improvement, in particular in view of the way the raw materials are introduced.

BRIEF DESCRIPTION

Disclosed herein are methods for producing aryl alkyl carbonate, methods for the production of polycarbonate, polycarbonates produced therefrom, and uses for an acetone monomer mixture.

In an embodiment, a method for producing an aryl alkyl carbonate can comprise: reacting methanol with a diaryl carbonate in the presence of a catalyst to form a mixture comprising an aryl alkyl carbonate and a hydroxy compound, wherein the methanol is in an acetone monomer mixture comprising acetone and at least one of diaryl carbonate and dihydroxy compound; separating the aryl alkyl carbonate from the mixture.

In an embodiment, a method for producing polycarbonate by melt polymerization can comprise: adding acetone, diaryl carbonate, and dihydroxy compound to a melt polymerization unit, wherein the acetone is added to the melt polymerization unit as a mixture with the diaryl carbonate and/or the dihydroxy compound; melt polymerizing the dihydroxy compound and the diaryl carbonate to produce the polycarbonate; recovering a recovered acetone from the melt polymerization unit; adding the recovered acetone to a reaction vessel, wherein the recovered acetone in the reaction vessel has one or more of a methanol content of less than or equal to 100 ppm, and a ketone and aldehyde content of less than or equal to 100 ppm; reacting the recovered acetone to produce a second dihydroxy compound; and adding the second dihydroxy compound to the melt polymerization unit.

In another embodiment, a method for producing polycarbonate by melt polymerization can comprise: separating acetone from an acetone monomer mixture to form a separated acetone and a separated monomer; adding the separated monomer and a second monomer to a melt polymerization unit, wherein the separated monomer comprises a dihydroxy compound and the second monomer comprises a diaryl carbonate or separated monomer comprises the diaryl carbonate and the second monomer comprises the dihydroxy compound; melt polymerizing the dihydroxy compound and the diaryl carbonate to produce the polycarbonate; adding the separated acetone to a reaction vessel, wherein the separated acetone in the reaction vessel has one or more of a methanol content of less than or equal to 100 ppm, and a ketone and aldehyde content of less than or equal to 100 ppm; reacting the separated acetone with a monohydroxy compound to produce a second dihydroxy compound; and adding the second dihydroxy compound to the melt polymerization unit.

In an embodiment, an integrated method for producing a polycarbonate can comprise: making an acetone monomer mixture comprising a monomer and acetone, wherein the acetone and/or the monomer has one or more of a methanol content of less than or equal to 100 ppm, and a ketone and aldehyde content of less than or equal to 100 ppm; transporting the acetone monomer mixture to a polycarbonate production plant; reacting the monomer and a second monomer to produce the polycarbonate, wherein the monomer comprises a dihydroxy compound and the second monomer comprises a diaryl carbonate or monomer comprises the diaryl carbonate and the second monomer comprises the dihydroxy compound; separating a separated acetone from the acetone monomer mixture prior to the reacting and/or recovering a recovered acetone during the reacting; adding the separated acetone and/or the recovered acetone to a reaction vessel; reacting the separated acetone and/or the recovered acetone to produce a second dihydroxy compound; and adding the second dihydroxy compound to the melt polymerization unit.

The above described and other features are exemplified by the Figures and the following detailed description.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Processes for polymerizing polycarbonate require that large amounts of separate raw materials be produced, transported, and/or stored, or that several large production units are combined on a single production site. Most of the raw materials used in polycarbonate production are solids at ambient temperature, which implies that if large amounts of these materials are transported, a number of problems arise that adversely affect the overall process, e.g., the economics. If the materials are to be shipped in the molten state, a large amount of energy is required to maintain the high temperatures, while solidifying the materials after their production requires large, complicated equipment such as cooling bands and/or prill towers. Such equipment unnecessarily increases the capital investment, and is also expensive and energy consuming to operate.

One method of transporting reactant monomers for polycarbonate production involves transporting one or more monomers, such as diphenyl carbonate and bisphenol A, in liquid phase with acetone (e.g., wherein the phase is based upon the amount of acetone present), hereinafter referred to as an acetone monomer mixture. The acetone monomer mixture can first be separated into the monomer and a separated acetone or the acetone monomer mixture can be added directly to the polymerization process, which can optionally comprise a step of recovering acetone (hereinafter also referred to as recovered acetone), which can then be used in the formation of a dihydroxy compound. For example, the recovered acetone can be reacted with phenol to form bisphenol A that can be used, for example, in the polycarbonate polymerization.

It was further discovered that when an acetone monomer mixture that comprises at least one of alcohol(s), aldehyde(s), and ketone(s) (other than acetone) is directly used in a polycarbonate polymerization, the subsequent production of a dihydroxy compound using the recovered acetone resulted in a higher occurrence of side reactions. In other words, it was discovered that when an acetone monomer mixture that comprises one or more of: an alcohol (such as methanol, ethanol, propanol, butanol, and the like), an aldehyde (such as methanal, ethanal, propanal, butanal, and the like), or a ketone other than acetone (such as methyl isobutyl ketone (MIBK), benzophenone, cyclohexanone, acetophenone, butanone, diethyl ketone, and the like) is directly used in a polycarbonate polymerization, for example, that any subsequent production of a dihydroxy compound using the recovered acetone was worsened due to the higher occurrence of side reactions. For example, aldehydes and ketones can react in the dihydroxy compound reaction to form various bisphenol analogs and by-products that disadvantageously reduce product purity and have a negative impact on color of the dihydroxy compound and final color quality of the polycarbonate through the formation of species that can easily be oxidized. Regarding the alcohol, the alcohol can react, for example, with a mercapto copromoter system that is often used in the production of a dihydroxy compound as part of the catalyst system. The mercapto copromoter system can be present in bulk (as an additive) or can be ionically bound to the base resin catalyst material.

It was discovered that the problems arising during the subsequent production of a dihydroxy compound could be reduced by reducing the total amount of alcohol, specifically, methanol, to less than 100 parts per million by weight (ppm), specifically, less than or equal to 10 ppm, more specifically, less than or equal to 1 ppm based on the total weight of the acetone; reducing the total amount of aldehydes and ketones to less than or equal to 100 ppm, specifically, to less than or equal to 10 ppm, more specifically, to less than or equal to 1 ppm based on the total weight of the acetone; or a combination comprising one or both of the foregoing. The step of reducing one or more of the alcohol, the aldehyde, and the ketone can occur prior to formation of the acetone monomer mixture; and/or prior to addition of the acetone monomer mixture to the polycarbonate polymerization; and/or after removal of the recovered acetone from the melt polymerization and prior to reacting the recovered acetone to form a dihydroxy compound.

The Applicants further discovered that the problems arising during the subsequent production of a dihydroxy compound could be reduced by reducing the metal content. The metal can arise from, for example, a metal catalyst used to catalyze a reaction, metal ions from reactor and/or conduit materials (e.g., steel (such as iron, chromium, nickel, and molybdenum)), metal ions present in water used in a reaction (such as sodium, calcium, and magnesium), or a combination comprising one or more of the foregoing. The metal in the acetone used in the formation of the dihydroxy compound can be such that the resultant dihydroxy compound comprises, less than or equal to 38 parts per billion by weight (ppb), specifically, less than or equal to 23 ppb of molybdenum; less than or equal to 38 ppb, specifically, less than or equal to 23 ppb vanadium; less than or equal to 38 ppb, specifically, less than or equal to 23 ppb chromium; less than or equal to 85 ppb, specifically, less than or equal to 57 ppb titanium; less than or equal to 425 ppb, specifically, less than or equal to 284 ppb of niobium; less than or equal to 38 ppb, specifically, less than or equal to 23 ppb of nickel; less than or equal to 12 ppb, specifically, less than or equal to 6 ppb zirconium; less than or equal to 12 ppb, specifically, less than or equal to 6 ppb of iron, or a combination comprising one or more of the foregoing based on the total amount of the dihydroxy compound.

A reduced metal content can result in a polycarbonate with a low color value of, for example, a CIE b* index of less than or equal to 0.5, specifically, less than or equal to 0.15 as determined by spectrophotometry and high light transmission of, for example, greater than or equal to 89% as determined by spectrophotometry. The polycarbonate can have a light transparency of greater than 90% as determined using 3.2 mm thick samples using ASTM D1003-00, Procedure B using CIE standard illuminant C, with unidirectional viewing. Accordingly, when the polycarbonate has such a light transparency, it is herein referred to as an "optical grade" polycarbonate.

The acetone monomer mixture can comprise acetone and at least one monomer. For example, the monomer can comprise a dihydroxy compound (such as bisphenol A), a diaryl carbonate (such as diphenyl carbonate), or a combination comprising one or both of the foregoing. The acetone and the monomer can be present in a molar ratio of greater than or equal to 0.5:1, specifically, greater than or equal to 0.6:1, more specifically, greater than or equal to 0.8:1, even more specifically, greater than or equal to 0.9:1. The acetone monomer mixture can comprise acetone and the monomer in a molar ratio of less than or equal to 5:1, specifically, less than or equal to 3.5:1, more specifically, less than or equal to 3, even more specifically, less than or equal to 2.5, still more specifically, less than or equal to 2:1. The acetone monomer mixture can comprise acetone and the monomer in a molar ratio of 0.5:1 to 7:1, specifically, 0.5:1 to 5:1, more specifically, 0.5:1 to 3:1, even more specifically, 1:1 to 3:1. The acetone monomer mixture can comprise 1 to 90 weight percent (wt %), specifically, greater than 3 to 90 wt %, more specifically, 20 to 80 wt %, more specifically, 25 to 65 wt % of the acetone based on the total weight of the acetone monomer mixture.

The acetone monomer mixture can further comprise an aryl alcohol. For example, the acetone monomer mixture can comprise 0 to 10 wt % of aryl alcohol, specifically, 1 to 8 wt % of aryl alcohol, more specifically, 1.5 to 5 wt % aryl alcohol based on the total weight of the acetone monomer mixture. Accordingly, any residual aryl alcohol from the production of the diaryl carbonate can be present in the acetone monomer mixture. For example, the acetone monomer mixture can comprise less than or equal to 500 ppm, specifically, less than or equal to 400 ppm of phenol based on the total amount of acetone monomer mixture.

The acetone monomer mixture can be made by combining the monomer and the acetone at the monomer production site, for example, by adding the acetone to a stirred vessel containing the liquid monomer, or by adding the liquid monomer to the acetone, until the desired acetone/monomer ratio is obtained. The liquid monomer can be the direct product mixture from the monomer reaction. Conversely, the monomer product mixture can be purified prior to mixing with the acetone.

In order to avoid hydrolysis of the monomer, for example, of a diaryl carbonate, the acetone monomer mixture can be free of water. For example, the acetone monomer mixture can comprise less than or equal to 1 wt % water, specifically 0 to 0.3 wt % based on the total weight of the acetone monomer mixture.

Prior to forming the acetone monomer mixture, the acetone can be purified. Acetone purification (also referred to as an alcohol purification reaction) can be performed by reacting an alcohol, such as methanol, ethanol, and the like, present in the acetone with an amount of a diaryl carbonate such as a diaryl carbonate of the formula (I) below, for example, diphenyl carbonate, bismethyl salicyl carbonate, an activated diaryl carbonate, and the like to yield an aryl alkyl carbonate and a hydroxy compound. For example, methanol present in the acetone can react with diphenyl carbonate to form phenyl methyl carbonate and phenol. This reaction can be performed in the presence of a transesterification catalyst. As the reaction products, for example, phenyl methyl carbonate and phenol are less volatile than methanol, they are more easily separated from the acetone, for example, by distillation or flash separation.

The alcohol reduction reaction can be performed at a molar ratio of diaryl carbonate to alcohol of greater than or equal to 1, specifically, greater than or equal to 2, more specifically, greater than or equal to 5, more specifically, greater than or equal to 10. The alcohol reduction reaction can be performed at a temperature of greater than or equal to 50° C., specifically, greater than or equal to 100° C., more specifically, greater than or equal to 130° C., even more specifically, greater than or equal to 145° C. The alcohol reduction reaction can be performed at a ratio of mmol of TMAOH/mol methanol of greater than or equal to 2, specifically, greater than or equal to 5, more specifically, greater than or equal to 9, or 2 to 30 or 5 to 30. The concentration of the catalyst in water can be greater than 0.1 wt %, specifically, greater than or equal to 1 wt %, more specifically, greater than or equal to 10 wt %, or 0.1 wt % to 10 wt %, or 10 to 20 wt %.

The transesterification catalyst can comprise an acidic catalyst, for example, with or without a mercapto copromoter system. The transesterification catalyst can comprise a basic catalyst, for example, a quaternary ammonium compound, a quaternary phosphonium compound, or a combination comprising at least one of the foregoing. The transesterification catalyst can comprise tetramethyl ammonium hydroxide (TMAOH). The alcohol reduction reaction can be performed at a molar ratio of tranesterification catalyst to alcohol of greater than or equal to 1, specifically, greater than or equal to 2, more specifically, greater than or equal to 5, even more specifically, greater than or equal to 10.

The monomer can comprise a dihydroxy compound of the formula HO—$R^1$—OH, in which the $R^1$ groups contain aliphatic, alicyclic, and/or or aromatic moieties. The dihydroxy monomer can comprise a dihydroxy monomer of formula (2)

$$HO\text{-}A^1\text{-}Y^1\text{-}A^2\text{-}OH \quad (2)$$

wherein each of $A^1$ and $A^2$ is a monocyclic divalent aromatic group and $Y^1$ is a single bond or a bridging group having one or more atoms that separate $A^1$ from $A^2$.

The monomer can comprise a diaryl carbonate of the formula (I)

wherein n is an integer 1 to 3 and each $R_2$ is independently linear or branched; optionally substituted; $C_{1-34}$ alkyl, specifically, $C_{1-6}$ alkyl, more specifically, $C_{1-4}$ alkyl; $C_{1-34}$alkoxy, specifically, $C_{1-6}$ alkoxy, more specifically, $C_{1-4}$ alkoxy; $C_{5-34}$ cycloalkyl; $C_{7-34}$ alkylaryl; $C_{6-34}$ aryl; or a halogen radical, specifically, a chlorine radical. $R_2$ can also represent —COO—R', wherein R' can be H; $C_{1-34}$ alkyl, specifically, $C_{1-6}$ alkyl, more specifically, $C_{1-4}$ alkyl; $C_{1-34}$ alkoxy, specifically, $C_{1-16}$ alkoxy, specifically, $C_{1-4}$ alkoxy; $C_{5-34}$ cycloalkyl; $C_{7-34}$ alkylaryl; or $C_{6-34}$ aryl. The diaryl carbonate can comprise diphenyl carbonate.

There are several methods by which diaryl carbonate can be produced. One method for producing diaryl carbonate includes decarbonylating a diaryl oxalate (such as diphenyl oxalate) in the presence of a decarbonylation catalyst while removing a carbon monoxide by product. The decarbonylation reaction can occur in the liquid phase. The diaryl oxalate can comprise a diaryl oxalate of the formula: ArO(C=O)—(C=O)OAr, where each Ar independently can be an aromatic hydrocarbon group having 6 to 14 carbon atoms, for example, Ar can be a phenyl group, which can be substituted with at least one selected from alkyl groups having 1 to 6 carbon atoms (such as methyl, ethyl, propyl, butyl, pentyl, and hexyl), alkoxy groups having 1 to 6 carbon atoms (such as methoxy, propoxy, butoxy, pentoxy, and hexoxy), and halogen atoms (such as fluorine, chlorine, bromine, and iodine). The diaryl oxalate can comprise diphenyl oxalate, m-cresyl oxalate, m-cresyl phenyl oxalate, p-cresyl oxalate, p-cresyl phenyl oxalate, dinaphthyl oxalate, bis(diphenyl)oxalate, bis(chlorophenyl)oxalate, or a combination comprising one or more of the forgoing. The diaryl oxalate can contain less than or equal to 5 parts per million by weight (ppm), specifically, less than or equal to 2 ppm of a hydrolysable halogen.

The diaryl oxalate can be prepared by transesterifying a dialkyl oxalate (such as dimethyl oxalate) with a hydroxyaryl compound (such as phenol) in the presence of a transesterification catalyst, where the transesterification reaction can occur in the liquid phase. The dialkyl oxalate can comprise one or more lower dialkyl oxalates of which the alkyl group comprises 1 to 6 carbon atoms, for example, dimethyl oxalate, diethyl oxalate, dipropyl oxalate, dibutyl oxalate, dipentyl oxalate, and dihexyl oxalate.

The transesterification catalyst used for the preparation of the diaryl oxalate from the dialkyl oxalate and the hydroxyaryl compound can comprise at least one of, for example, compounds and complexes of alkali metals, compounds and complexes of cadmium and zirconium, lead-containing compounds, iron-containing compounds, copper group metal compounds, silver-containing compounds, zinc-containing compounds, organic tin compounds, and Lewis acid compounds of aluminum, titanium, and vanadium. The decarbonylation catalyst can comprise at least one organic phosphorus compound (such as an organic phosphine compound, an organic phosphine oxide compound, an organic phosphine dihalide compound, and an organic phosphonium salt compound). The decarbonylation catalyst can contain a halogen, for example, on the phosphorus containing compound or as a separate halogen compound.

Another method for producing diaryl carbonate includes reacting an aromatic hydroxy compound and carbon monoxide in the presence of oxygen, where the reaction can be facilitated by a catalyst and an optional organic salt. For example, the reaction can be the oxidative carbonylation of phenol, where the reaction can occur in a fixed-bed reactor or in an autoclave reactor. Suitable catalysts for the oxidative carbonylation of aromatic hydroxy compounds include a palladium catalyst. The palladium catalyst can be in solvated form (such as $PdBr_2$ promoted with transition metal oxides and solvated promoters, including one or more of $N(Bu)_4Br$, $Mn(AcAc)_2$, $NaO(C_6H_5)$ and the like), suspended form with Pd supported on pulverized $TiO_2$, or extrudate form with Pd supported on rare earth metal oxide. The palladium catalyst can comprise $Pd(OAc)_2$/hydrotalcite. As used herein, Bu means butyl, AcAc means acetylacetonate, and OAc means acetate. The catalyst can comprise a cocatalyst, such as a cesium compound, a manganese compound, a cobalt compound, a copper compound, hydroquinone, benzoquinone, naphthoquinone, or a combination comprising one or more of the foregoing. The organic salt can comprise, for example, $^nBu_4NBr$, $^nBu_4PBr$, PPNBr, and the like.

The aromatic hydroxy compound can comprise an aromatic hydroxy compound of the formula (III)

(III)

wherein n and $R_2$ are defined as above in formula (I). The aromatic hydroxy compound can comprise phenol, 4-tert-butylphenol, biphenyl-4-ol, 4-(1-methyl-1-phenylethyl)-phenol, or a combination comprising one or more of the foregoing.

Other methods for producing diaryl carbonate can be found in U.S. Pat. Nos. 5,922,827, 6,265,524, 5,831,111, and 5,710,310 and include reacting an aromatic hydroxy compound, which can comprise the aromatic hydroxy compound of formula III, with phosgene in either the gas or liquid phase, for example, the direct phosgenation of phenol and reacting an aromatic hydroxy compound with a dialkyl carbonate, where said reactions can occur in the presence of a transesterification catalyst. The aromatic hydroxy compound and either phosgene or the dialkyl carbonate can be added in a molar ratio of 1:0.1 to 1:10, specifically, 1:0.2 to 1:5, more specifically, 1:0.5 to 1:3. The indicated molar ratio does not take into account any recycled components that can be added back to the production column.

The dialkyl carbonate can comprise the dialkyl carbonate of the formula (II)

(II)

wherein each $R_1$ independently is linear or branched; optionally substituted; $C_{1-34}$ alkyl, specifically, $C_{1-6}$ alkyl, more specifically, $C_{1-4}$ alkyl.

The dialkyl carbonates can comprise dimethyl carbonate, diethyl carbonate, dipropyl carbonate (e.g., di(n-propyl) carbonate, and/or di(isopropyl) carbonate), dibutyl carbonate (e.g., di(n-butyl) carbonate, di(sec-butyl) carbonate, and/or di(tert-butyl) carbonate), dihexyl carbonate, or a combination comprising one or more of the foregoing.

A catalyst can be used to facilitate the reaction between the aromatic hydroxy compound and either phosgene or the dialkyl carbonate. The catalyst can be a homogeneous catalyst and/or a heterogeneous catalyst (wherein a heterogeneous catalyst comprises two or more catalysts), known to facilitate this reaction. The catalyst can comprise hydrides, oxides, hydroxides, alcoholates, amides and other salts of alkali and alkaline earth metals, such as of lithium, sodium, potassium, rubidium, cesium, magnesium and calcium, specifically, lithium, sodium, potassium, magnesium, calcium, or a combination comprising one or more of the foregoing. Further catalyst can include metals (such as titanium, lead, tin, zirconium, molybdenum, niobium, vanadium, uranium, iron, zinc, aluminum, yttrium, lanthanum, hafnium, tungsten, neodymium, samarium, ytterbium, copper, or a combination comprising one or more of the foregoing), organotin compounds, lead compounds, polymeric tin compounds, a combination comprising one or more of the foregoing. Some examples of catalyst are set forth in U.S. Pat. No. 5,831,111.

The catalyst, when homogeneous, can be introduced to the reaction mixture in dissolved or suspended form together with the stream containing the aromatic hydroxy compound. Alternatively, the catalyst can be introduced, for example, in the reaction alcohol or an inert solvent. A heterogeneous catalyst can be used in a packed bed, a column, or in special catalytic distillation arrangements, as well as in other arrangements.

The diaryl carbonate can be purified to produce a purified diaryl carbonate comprising a metal. The metal can comprise titanium, lead, tin, zirconium, molybdenum, niobium, vanadium, iron, zinc, aluminum, yttrium, lanthanum, hafnium, tungsten, neodymium, samarium, ytterbium, copper, chromium, nickel, manganese, bismuth, niobium, or a combination comprising one or more of the foregoing.

The purified diaryl carbonate can comprise less than or equal to 38 parts per billion by weight (ppb), specifically, less than or equal to 23 ppb of molybdenum; less than or equal to 38 ppb, specifically, less than or equal to 23 ppb vanadium; less than or equal to 38 ppb, specifically, less than or equal to 23 ppb chromium; less than or equal to 85 ppb, specifically, less than or equal to 57 ppb titanium; less than or equal to 425 ppb, specifically, less than or equal to 284 ppb of niobium; less than or equal to 38 ppb, specifically, less than or equal to 23 ppb of nickel; less than or equal to 12 ppb, specifically, less than or equal to 6 ppb zirconium;

less than or equal to 12 ppb, specifically, less than or equal to 6 ppb of iron, or a combination comprising one or more of the foregoing.

The metal content in the diaryl carbonate can be reduced by introducing an aqueous stream to a diaryl carbonate stream that comprises a metal such that the metal can be precipitated to its oxide and/or hydroxide form. The aqueous stream can be introduced such that greater than or equal to 100 ppm, specifically, 100 to 10,000 ppm, more specifically, 200 to 8,000 ppm, even more specifically, 500 to 7,000 ppm, e.g., 1,000 to 7,000 ppm, of water is introduced based on the total weight of the diaryl carbonate stream and the aqueous stream. The aqueous stream can comprise sodium bicarbonate (or other salts of the alkali and alkaline earth metals such as carbonates or hydrogen carbonates, phosphates, hydrogen phosphates, borates, acetates, propionates) in addition to water.

The introduction of the aqueous stream can occur at a temperature of greater than or equal to the melting point of the diaryl carbonate in order to ensure that the diaryl carbonate is a molten diaryl carbonate. Further increasing the temperature to a temperature greater than the melting point of the diaryl carbonate, for example, to a temperature of greater than 100 degrees Celsius (° C.), can reduce the viscosity of the molten diaryl carbonate. The introduction of the aqueous stream can occur at a temperature of greater than or equal to 80° C., specifically, greater than or equal to 90° C., more specifically, greater than 100° C., even more specifically, 110 to 250° C., still more specifically, 120 to 250° C.

The introduction of the aqueous stream can occur in the presence of a solvent, e.g., 0 to 50 wt % (e.g., greater than zero up to 50 wt %), specifically, 0 to 25 wt %, more specifically, 0 to 1 wt %, even more specifically, 0 wt % of a solvent based on the total weight of the diaryl carbonate stream and the aqueous stream. For example, the diaryl carbonate stream can be free of any added solvent (e.g., no solvent is added to the diaryl carbonate stream prior to the introduction of the aqueous stream). Examples of solvents include aliphatic hydrocarbons (such as pentane, petroleum ether, cyclohexane, and isooctane), aromatic hydrocarbons (such as benzene, toluene, and xylene), chloroaromatic compounds (such as chlorobenzene and dichlorobenzene), ethers (such as dioxane, tetrahydrofuran, tert-butyl methyl ether, and anisole), amides (such as dimethylacetamide and N-methyl-pyrrolidinone), and alcohols (such as tert-butanol, cumyl alcohol, isoamyl alcohol, diethylene glycol, and tetramethylurea).

The introduction of the aqueous stream can be facilitated by the use of a device that is capable of facilitating the contact between the diaryl carbonate stream and water in order to achieve the hydrolysis reaction of the metal, e.g., a mixing device.

Once the metal is precipitated, it can then be easily separated by a separation process utilizing one or both of a separation column and a filter to result in a purified diaryl carbonate. When both a separation column and a filter are used, the filter can be upstream of the separation column and/or down stream of separation column. If multiple separation columns are present, a filter can be present upstream and/or downstream of one or more of the separation columns.

When the separation process utilizes a separation column, the separation column can be a distillation column, a reactive distillation column, a catalytic distillation column, or the like. The column can contain concentrating part(s) in the upper portion of the separation column and zone(s) beneath the concentrating part, which can have at least two sections, wherein concentrating part(s) of the separation column can be equipped with intermediate condenser(s). Each of the sections, independently of the others, can have 5 or greater, specifically, 10 or greater theoretical equilibrium stages. At the top of the separation column, the reflux stream can be condensed in a condenser, wherein at least a portion of the condensed vapor can re-enter the separation column. At the bottom of the separation column, the bottom stream can be heated in a reboiler, wherein at least a portion of the heated bottom stream can re-enter the separation column. The aqueous stream can be introduced to the diaryl carbonate stream in a mixing device that is located upstream of the separation column and/or that is located downstream of the condenser and upstream of the separation column. When a mixing device is located downstream of the condenser and upstream of the separation column, the aqueous stream and the diaryl carbonate stream, that is the portion of the reflux stream (also referred to as a top stream first portion) to be reintroduced, are introduced to the mixing device, mixed, and introduced to the separation column. The separation column can comprise a set of cascading separation columns to obtain even higher purity DPC.

When the separation process utilizes a filter, the mesh size of the filter can be less than or equal to 20 micrometers, specifically, less than or equal to 1 micrometer, more specifically, less than or equal to 0.2 micrometers.

The residual water in the purified diaryl carbonate can be less than or equal to 1,000 ppm, specifically, less than or equal to 500 ppm, more specifically, less than or equal to 100 ppm.

The acetone monomer mixture can be transported to a polycarbonate production plant. Storage and transport vessels include vessels such as road and rail tankers, bulk containers, tank barges and tank ships, storage tanks, drums and pipelines.

The acetone monomer mixture can be maintained at a transport temperature of 20 to 70° C., specifically, 20 to 50° C. The transport temperature can be maintained at plus or minus 10° C., specifically, plus or minus 5° C. of a set transport temperature. If the acetone monomer mixture is transported at a temperature greater than the ambient temperature, the transport and storage vessels can be insulated to reduce heat loss, and equipped with the necessary safety devices required.

During storage and transport, additional acetone can be added to the acetone monomer mixture or an amount of acetone can be removed, for example, to adjust the molar ratio of the monomer to the acetone. For example, additional acetone can be added to compensate for losses, for example, due to evaporation.

Upon arrival at the polycarbonate production facility, the acetone monomer mixture can be separated into the monomer and the acetone (also referred to as separated acetone) or the acetone monomer mixture can be directly added to the melt polymerization. The acetone monomer mixture can be separated by, for example, distillation (such as flash distillation, continuous distillation, or a combination comprising one or both of the foregoing), evaporation (such as in a continuous film evaporator), or a combination comprising one or both of the foregoing. When the acetone monomer mixture is added directly to the melt polymerization, acetone can be removed (also referred to as recovered acetone) from the melt polymerization. Alcohol present in the separated acetone and/or the recovered acetone can be removed as described above prior to use in a dihydroxy compound formation reaction.

Figure 1:
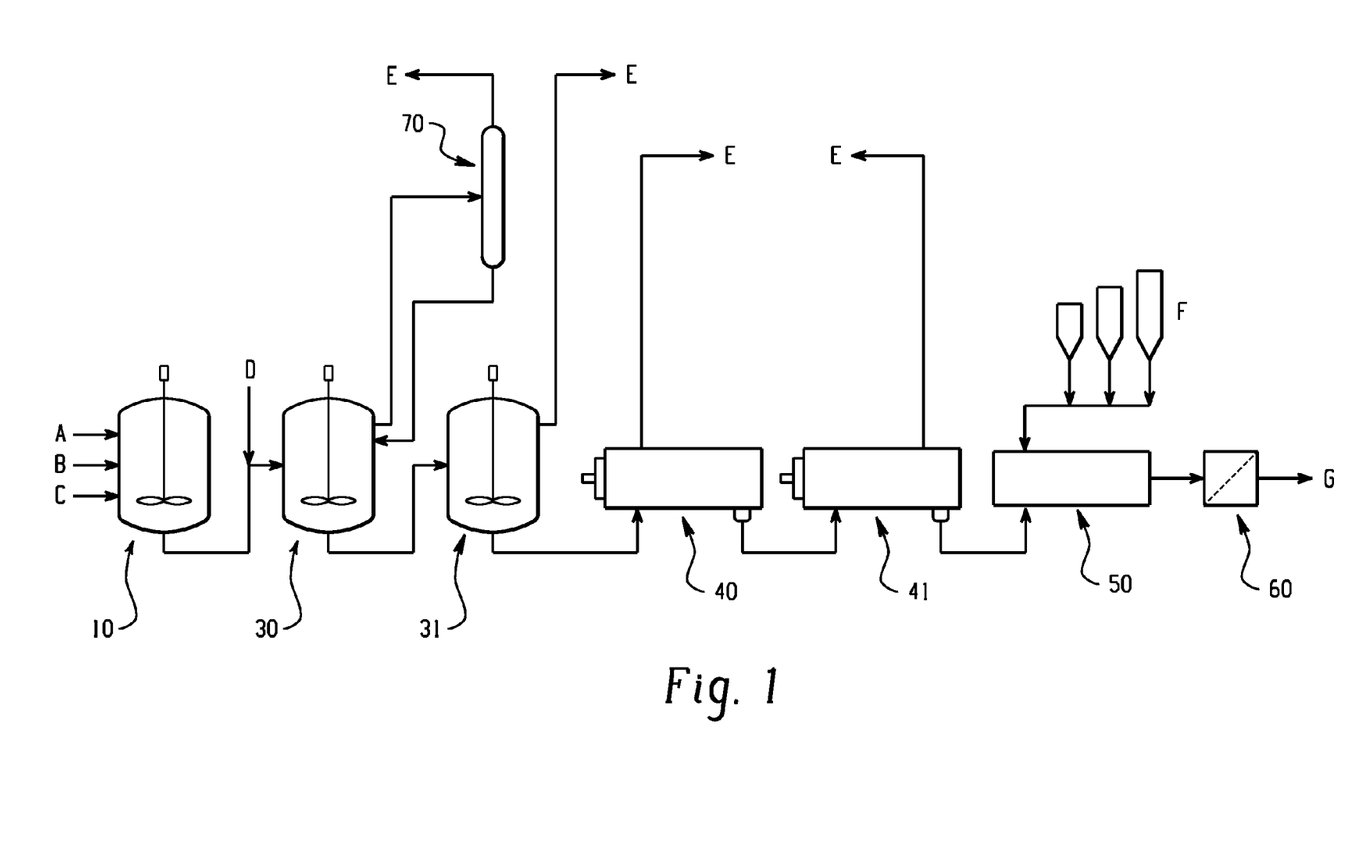
FIG. 1 is an illustration of a melt polymerization where the reactants are added to a mixer in a polymerization unit.
Figure 2:
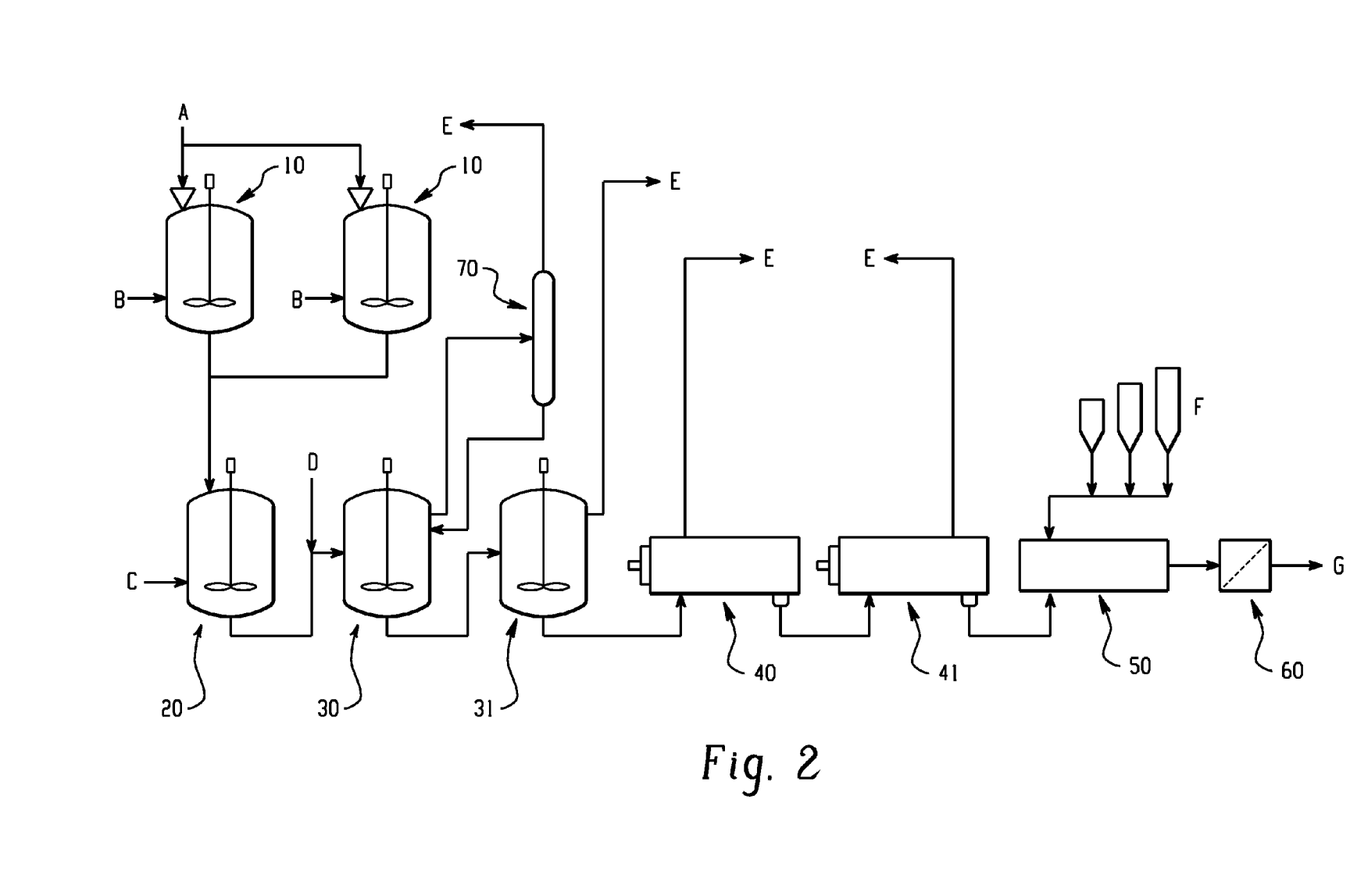
FIG. 2 is an illustration of a melt polymerization where the reactants are first added to two separate mixers in a polymerization unit.

The polymerization can occur in a polymerization unit; two exemplary polymerization units are illustrated in FIG. 1 and FIG. 2. The polymerization unit can comprise pre-mixer 10, buffer unit 20, oligomerization units 30 and 31, polymerization units 40 and 41, extruder 50, filter 60, scrubber 70, or a combination comprising one or more of the foregoing. In FIG. 1 dihydroxy compound A, carbonate compound B, and catalyst C are added to pre-mixer 10. Additional monomer D can optionally be added and the reactants are sent to oligomerization unit 30. Phenol by-product E is removed from oligomerization units 30 and 31 and from polymerization units 40 and 41. Additive F is added to the polymerized polycarbonate in extruder 50. The extruded polycarbonate is filtered in melt filter 60 to produce polycarbonate pellets G. FIG. 2 illustrates a similar polymerization unit except that dihydroxy compound A and carbonate compound B are added to two separate pre-mixers 10 and 11 that can operate sequentially in batch mode and are fed into buffer unit 20, where catalyst C is added. The dihydroxy compound and/or the carbonate compound can be added to the polymerization unit as a monomer mixture with acetone, for example, as A', B', or D'.

As acetone can be recovered from the polymerization unit (e.g., acetone can be recovered after the polycarbonate has been formed), the acetone does not need to be pre-separated prior to the addition of acetone monomer mixture. As used herein, "not separated" refers to the acetone remaining in the vessel comprising the acetone monomer mixture. In other words, although the acetone may be present in a liquid or gaseous phase in the vessel, it does not have to be withdrawn from the vessel, e.g., prior to the addition of the catalyst.

Acetone can be recovered in the polymerization due to the differences in volatilities between the dihydroxy reactant, the carbonate compound, the phenol byproduct, and the polymerized product at the operating conditions used in the polymerization unit (150° C.<Temperature<320° C., 0.3 millibars absolute (mbara)<Pressure<atmospheric). As such, acetone can be recovered after the melt polymerization reaction forming the polycarbonate, e.g., from different sections of the polymerization unit. The separation device utilized to remove the acetone can be selected to avoid the loss of unreacted diaryl carbonate ester and any other volatile components from the reaction mixture. The separation device can comprise single or multiple separation steps located after the polymerization unit.

Likewise, the phenol by-product can be recovered. The phenol by-product can be recovered in the same separation step(s) as the acetone separation and/or in a separate separation step(s). When the phenol by-product and the acetone are separated in a same separation step, they can be removed in the same product stream and optionally separated, or can be reacted to produce additional dihydroxy reactant.

Figure 3:
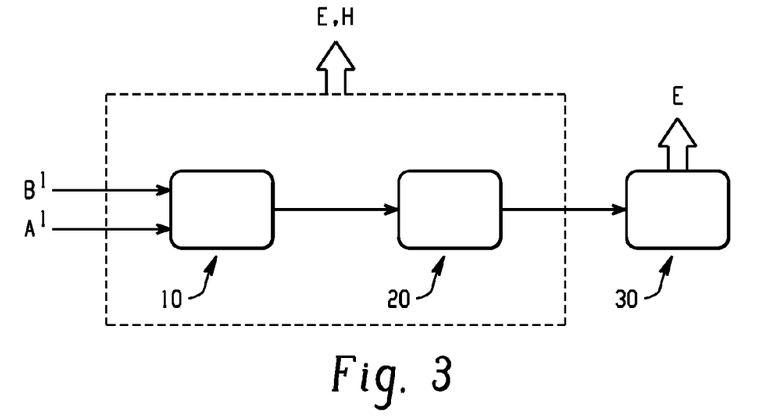
FIGS. 3-5 are illustrations of a melt polymerization where an acetone monomer mixture is added to the polymerization unit.
Figure 4:
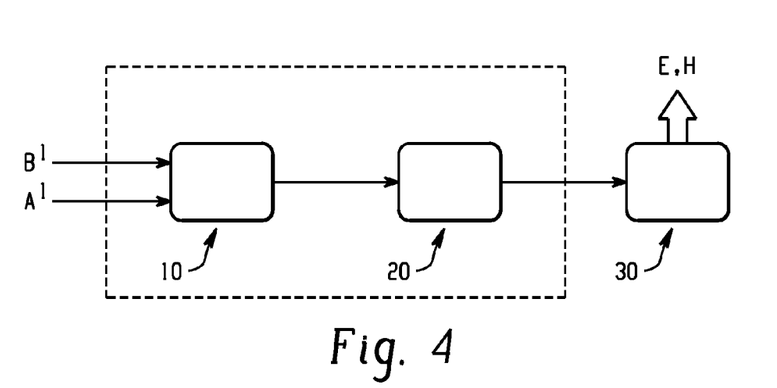
Figure 5:
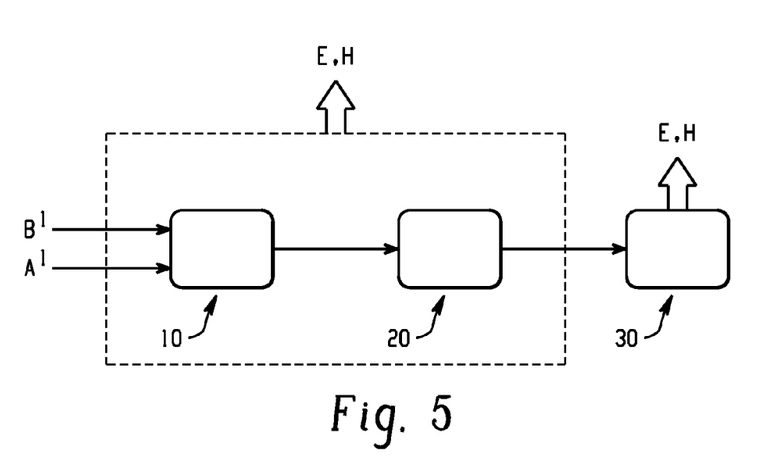

FIGS. 3-5 illustrate different manners in which recovered acetone H and/or phenol by-product E can be removed. FIG. 3 illustrates a first removal option, wherein recovered acetone H and/or phenol by-product E are recovered from pre-mixer 10 and/or buffer unit 20. The recovery can occur based on selecting a combination of temperature and pressure in pre-mixer 10 and/or buffer unit 20 that allows for the devolatilization of recovered acetone H and/or phenol by-product E from the monomer mixture. For example, the conditions for such a removal can be at a temperature of 160 to 180° C. and atmospheric pressure and can result in greater than or equal to 95 wt % of the acetone H.

FIG. 4 illustrates a second removal option, wherein recovered acetone H and/or phenol by-product E can be recovered in the first oligomerization unit 30, where recovered acetone H can be recovered together with phenol by-product E, or as an independent stream. In order to prevent recovered acetone H and/or other monomers like A or B from leaving the monomer mixture prior to entering the oligomerization unit 30, the pressure can be increased to greater than atmospheric pressure in the stage(s) prior to oligomerization unit 30.

FIG. 5 illustrates a third removal option, wherein recovered acetone H and/or phenol by-product E is recovered from pre-mixer 10 and/or buffer unit 20 as well as in first oligomerization unit 30. Here, greater than or equal to 95 wt % of recovered acetone H can be recovered in pre-mixer 10 and/or a buffer unit 20 and from the first oligomerization unit 30. The relative removal percentages in pre-mixer 10 and/or buffer unit 20 and the oligomerization unit 30 can be adjusted depending on the operating conditions. For example, recovered acetone H removal in pre-mixer 10 and/or buffer unit 20 can be up to 95 wt % (e.g., greater than 0 to 95 wt %) of the total acetone in the acetone monomer mixture. The balance can optionally be removed in oligomerizer 30.

The separated acetone and/or the recovered acetone can be reacted with phenol, for example, a phenol byproduct from the polycarbonate polymerization, in the presence of a catalyst to produce a dihydroxy compound such as bisphenol A. The acetone for formation of the dihydroxy compound can comprise less than 100 ppm, specifically, less than or equal to 10 ppm, more specifically, less than or equal to 1 ppm of alcohol based on the total weight of acetone; less than or equal to 100 ppm, specifically, to less than or equal to 10 ppm, more specifically, to less than or equal to 1 ppm of a total amount of aldehydes and ketones to based on the total weight of the acetone; or a combination comprising one or both of the foregoing.

The dihydroxy compound formation reaction can be performed in the presence of a catalyst at a molar ratio of acetone to phenol of 1:2 to 1:20, specifically, 1:3 to 1:10. The catalyst can comprise a strong acid, for example, hydrochloric acid. The catalyst can comprise an ion exchange resin, for example, a sulfonated polystyrene resin. The ion exchange resin can comprise a copromoter such as mercapto copromoter system.

The resultant dihydroxy compound can have a metal content of less than or equal to 38 ppb, specifically, less than or equal to 23 ppb of molybdenum; less than or equal to 38 ppb, specifically, less than or equal to 23 ppb vanadium; less than or equal to 38 ppb, specifically, less than or equal to 23 ppb chromium; less than or equal to 85 ppb, specifically, less than or equal to 57 ppb titanium; less than or equal to 425 ppb, specifically, less than or equal to 284 ppb of niobium; less than or equal to 38 ppb, specifically, less than or equal to 23 ppb of nickel; less than or equal to 12 ppb, specifically, less than or equal to 6 ppb zirconium; less than or equal to 12 ppb, specifically, less than or equal to 6 ppb of iron, or a combination comprising one or more of the foregoing. Likewise, the metal content can be reduced to the reduced metal content by the method as described above prior to addition to the melt polymerization.

A "polycarbonate" means compositions having repeating structural carbonate units of formula (1)

(1)

in which the $R^1$ groups contain aliphatic, alicyclic, and/or or aromatic moieties (e.g., greater than or equal to 30 percent, specifically, greater than or equal to 60 percent, of the total number of $R^1$ groups can contain aromatic moieties and the balance thereof are aliphatic, alicyclic, or aromatic). Optionally, each $R^1$ can be a $C_{6-30}$ aromatic group, that is, can contain at least one aromatic moiety. $R^1$ can be derived from a dihydroxy compound of the formula HO—$R^1$—OH, in particular of formula (2)

$$HO\text{-}A^1\text{-}Y^1\text{-}A^2\text{-}OH \qquad (2)$$

wherein each of $A^1$ and $A^2$ is a monocyclic divalent aromatic group and $Y^1$ is a single bond or a bridging group having one or more atoms that separate $A^1$ from $A^2$. One atom can separate $A^1$ from $A^2$. Specifically, each $R^1$ can be derived from a dihydroxy aromatic compound of formula (3)

(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically, para) to each other on the $C_6$ arylene group. The bridging group $X^a$ can be single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. p and q can each be 1, and $R^a$ and $R^b$ are each a $C_{1-3}$ alkyl group, specifically, methyl, disposed meta to the hydroxy group on each arylene group.

$X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

$X^a$ can be a $C_{1-18}$ alkylene group, a $C_{3-18}$ cycloalkylene group, a fused $C_{6-18}$ cycloalkylene group, or a group of the formula —$B^1$-G-$B^2$— wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and i is 0, the ring as shown in formula (4) contains 4 carbon atoms, when k is 2, the ring as shown in formula (4) contains 5 carbon atoms, and when k is 3, the ring contains 6 carbon atoms. Two adjacent groups (e.g., $R^q$ and $R^t$ taken together) can form an aromatic group or $R^q$ and $R^t$ taken together can form one aromatic group and $R^r$ and $R^p$ taken together can form a second aromatic group. When $R^q$ and $R^t$ taken together form an aromatic group, $R^p$ can be a double-bonded oxygen atom, i.e., a ketone.

Bisphenols (4) can be used in the manufacture of polycarbonates containing phthalimidine carbonate units of formula (4a)

(4a)

wherein $R^a$, $R^b$, p, and q are as in formula (4), $R^3$ is each independently a $C_{1-6}$ alkyl group, j is 0 to 4, and $R_4$ is a $C_{1-6}$ alkyl, phenyl, or phenyl substituted with up to five $C_{1-6}$ alkyl groups. The phthalimidine carbonate units can be of formula (4b)

(4b)

wherein $R^5$ is hydrogen or a $C_{1-6}$ alkyl. $R^5$ can be hydrogen. Carbonate units (4a) wherein $R^5$ is hydrogen can be derived from 2-phenyl-3,3'-bis(4-hydroxy phenyl)phthalimidine (also known as N-phenyl phenolphthalein bisphenol, or "PPPBP") (also known as 3,3-bis(4-hydroxyphenyl)-2-phenylisoindolin-1-one).

Other bisphenol carbonate repeating units of this type are the isatin carbonate units of formula (4c) and (4d)

(4c)

(4d)

wherein $R^a$ and $R^b$ are each independently $C_{1-12}$ alkyl, p and q are each independently 0 to 4, and R' is $C_{1-12}$ alkyl, phenyl, optionally substituted with 1 5 to $C_{1-10}$ alkyl, or benzyl optionally substituted with 1 to 5 $C_{1-10}$ alkyl. $R^a$ and $R^b$ can each be methyl, p and q can each independently be 0 or 1, and R' can be $C_{1-4}$ alkyl or phenyl.

Examples of bisphenol carbonate units derived from bisphenols (4) wherein $X^b$ is a substituted or unsubstituted $C_{3-18}$ cycloalkylidene include the cyclohexylidene-bridged, alkyl-substituted bisphenol of formula (4e)

(4e)

wherein $R^a$ and $R^b$ are each independently $C_{1-12}$ alkyl, $R^g$ is $C_{1-12}$ alkyl, p and q are each independently 0 to 4, and t is 0 to 10. At least one of each of $R^a$ and $R^b$ can be disposed meta to the cyclohexylidene bridging group. $R^a$ and $R^b$ can each independently be $C_{1-4}$ alkyl, $R^g$ can be $C_{1-4}$ alkyl, p and q can each be 0 or 1, and t is 0 to 5. $R^a$, $R^b$, and $R^g$ can be each methyl, r and s can be each 0 or 1, and t can be 0 or 3, specifically, 0.

Examples of other bisphenol carbonate units derived from bisphenol (4) wherein $X^b$ is a substituted or unsubstituted $C_{3-18}$ cycloalkylidene include adamantyl units (4f) and units (4g)

(4f)

(4g)

wherein $R^a$ and $R^b$ are each independently $C_{1-12}$ alkyl, and p and q are each independently 1 to 4. At least one of each of $R^a$ and $R^b$ can be disposed meta to the cycloalkylidene bridging group. $R^a$ and $R^b$ can each independently be $C_{1-3}$ alkyl, and p and q can be each 0 or 1. $R^a$, $R^b$ can be each methyl, p and q can each be 0 or 1. Carbonates containing units (4a) to (4g) are useful for making polycarbonates with high glass transition temperatures (Tg) and high heat distortion temperatures.

Other possible aromatic dihydroxy compounds of the formula HO—$R^1$—OH include compounds of formula (6)

(6)

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. The halogen is usually bromine.

Some illustrative examples of specific aromatic dihydroxy compounds and bisphenol compounds of formula (3) are set for in U.S. Pat. No. 7,309,755

"Polycarbonates" includes homopolycarbonates (wherein each $R^1$ in the polymer is the same), copolymers comprising different $R^1$ moieties in the carbonate ("copolycarbonates"), copolymers comprising carbonate units and other types of polymer units, such as ester units, and combinations comprising at least one of homopolycarbonates and/or copolycarbonates.

The polycarbonate can be made by a melt polymerization process, which can be a continuous melt process. Generally, in a melt polymerization process, polycarbonates can be prepared by co-reacting, in a molten state, a dihydroxy compound and a diaryl carbonate, such as diphenyl carbonate. A useful melt process for making polycarbonates could also use a diaryl carbonate having electron-withdrawing substituents on the aryls. Examples of diaryl carbonates with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl) carbonate, bis(2-acetylphenyl) carboxylate, bis(4-acetylphenyl) carboxylate, or a combination comprising at least one of the foregoing esters. The diaryl carbonate to dihydroxy reactant can be present in a molar ratio of 2:1 to 1:2, specifically, in a molar ratio of 1.5:1 to 1:1.5, more specifically, in a molar ratio of 1.05:1 to 1:1.05, even more specifically, in a molar ratio of 1:1.

In addition, transesterification catalyst(s) can be employed. Transesterification catalysts used in the melt transesterification polymerization production of polycarbonates can include alpha and/or beta catalysts. Beta catalysts, which are organic transesterification catalysts, are typically volatile and degrade at elevated temperatures. Beta catalysts are therefore preferred for use at early low-temperature polymerization stages. Alpha catalysts, which are inorganic transesterification catalysts, are typically more thermally stable and less volatile than beta catalysts.

The alpha catalyst can comprise a source of alkali or alkaline earth ions. The sources of these ions include alkaline earth hydroxides such as magnesium hydroxide and calcium hydroxide. Sources of alkali metal ions can include the alkali metal hydroxides such as illustrated by lithium hydroxide, sodium hydroxide, potassium hydroxide, and combinations comprising at least one of the foregoing. Examples of alkaline earth metal hydroxides are calcium hydroxide, magnesium hydroxide, and combinations comprising at least one of the foregoing. Of these, sodium hydroxide is particularly desirable. The alpha catalyst typically will be used in an amount sufficient to provide $1\times10^{-2}$ to $1\times10^{-8}$ moles, specifically, $1\times10^{-4}$ to $1\times10^{-7}$ moles of metal hydroxide per mole of the dihydroxy compounds employed. Other possible sources of alkaline earth and alkali metal ions include salts of carboxylic acids (such as sodium acetate) and derivatives of ethylene diamine tetraacetic acid (EDTA) (such as EDTA tetrasodium salt, and EDTA magnesium disodium salt), as well as combinations comprising at least one of the foregoing. For example, the alpha catalyst can comprise alkali metal salt(s) of a carboxylic acid, alkaline earth metal salt(s) of a carboxylic acid, or a combination comprising at least one of the foregoing. In another example, the alpha catalyst comprises $Na_2Mg$ EDTA or a salt thereof.

The alpha transesterification catalyst can also, or alternatively, comprise salt(s) of a non-volatile inorganic acid. For example, the alpha catalyst can comprise salt(s) of a non-volatile inorganic acid such as $NaH_2PO_3$, $NaH_2PO_4$, $Na_2HPO_3$, $KH_2PO_4$, $CsH_2PO_4$, $Cs_2HPO_4$, and combinations comprising at least one of the foregoing. Alternatively, or in addition, the alpha transesterification catalyst can comprise mixed alkali metal salt(s) of phosphoric acid, such as $NaKHPO_4$, $CsNaHPO_4$, $CsKHPO_4$, and combinations comprising at least one of the foregoing.

Possible beta catalyst(s) can comprise a quaternary ammonium compound, a quaternary phosphonium compound, or a combination comprising at least one of the foregoing. The quaternary ammonium compound can be organic ammonium compound(s) having structure, wherein $R^{20}$-$R^{23}$ are independently a $C_1$-$C_{20}$ alkyl radical, $C_4$-$C_{20}$ cycloalkyl radical, or a $C_4$-$C_{20}$ aryl radical; and $X^-$ is an organic or inorganic anion. Optionally, anion $X^-$ can be selected from hydroxide, halide, carboxylate, sulfonate, sulfate, formate, carbonate, and bicarbonate. Some non-limiting examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often employed.

The quaternary phosphonium compound can be of organic phosphonium compounds having structure, wherein $R^{24}$-$R^{27}$ are independently a $C_1$-$C_{20}$ alkyl radical, $C_4$-$C_{20}$ cycloalkyl radical, or a $C_4$-$C_{20}$ aryl radical; and $X^-$ is an anion (e.g., an organic or inorganic anion). Optionally, anion $X^-$ can be selected from hydroxide, halide, alkoxide, aryloxide, carboxylate, sulfonate, sulfate, formate, carbonate, and bicarbonate. Where $X^-$ is a polyvalent anion such as carbonate or sulfate, it is understood that the positive and negative charges in the quaternary ammonium and phosphonium structures are properly balanced. For example, where $R^{20}$-$R^{23}$ are each methyl groups and $X^-$ is carbonate, it is understood that $X^-$ represents $2(CO_3^{-2})$.

Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate (TPPA), tetraphenyl phosphonium phenoxide (TPPP), and combinations comprising at least one of the foregoing. TBPA is often employed.

The amount of beta catalyst employed is typically based upon the total number of moles of dihydroxy compound employed in the polymerization reaction. When referring to the ratio of beta catalyst, for example, phosphonium salt, to all dihydroxy compounds employed in the polymerization reaction, it is convenient to refer to moles of phosphonium salt per mole of the dihydroxy compound(s), meaning the number of moles of phosphonium salt divided by the sum of the moles of each individual dihydroxy compound present in the reaction mixture. The amount of beta catalyst (e.g., organic ammonium or phosphonium salts) employed typically will be $1\times10^{-2}$ to $1\times10^{-5}$, specifically, $1\times10^{-3}$ to $1\times10^{-4}$ moles per total mole of the dihydroxy compounds in the reaction mixture.

Polycarbonates polymerized from such a purified diaryl carbonate can have a low color value of, for example, a CIE b* index of less than or equal to 0.5, specifically, less than or equal to 0.15 as determined by spectrophotometry and high light transmission of, for example, greater than or equal to 89% as determined by spectrophometry.

The polymerized polycarbonate can comprise less than or equal to 33 ppb, specifically, less than or equal to 20 ppb of molybdenum; less than or equal to 33 ppb, specifically, less than or equal to 20 ppb vanadium; less than or equal to 33 ppb, specifically, less than or equal to 20 ppb chromium; less than or equal to 75 ppb, specifically, less than or equal to 50 ppb titanium; less than or equal to 375 ppb, specifically, less than or equal to 250 ppb of niobium; less than or equal to 33 ppb, specifically, less than or equal to 20 ppb of nickel; less than or equal to 10 ppb, specifically, less than or equal to 5 ppb zirconium; less than or equal to 10 ppb, specifically, less than or equal to 5 ppb of iron, or a combination comprising one or more of the foregoing.

The following examples are provided to illustrate the present process. The examples are merely illustrative and are not intended to limit devices made in accordance with the disclosure to the materials, conditions, or process parameters set forth therein.

EXAMPLES

American Public Health Association (APHA) color values were determined using a Macbeth Spectrophotometer using a 10 wt % by volume solution of the dihydroxy compound in acetonitrile (ACN).

Polycarbonate Yellowness Index (YI) was measured in accordance with ASTM D1925.

Examples 1-11: Removal of Methanol from Acetone by Reaction with Diphenyl Carbonate A reaction mixture was introduced in a 150 cubic centimeter (cc), stainless steel stirred tank reactor. The reactor had a top manometer, internal temperature probe and depressurization valve. The reactor was placed on a hot plate with a magnetic stirrer so that an even temperature was controlled with the internal probe and continuous stirring. The reaction mixture comprised 50 grams (g) acetone, 500 ppm methanol, and varying amounts of diphenylcarbonate and TMAOH as catalyst as shown in Table 1 in order to demonstrate the removal of methanol by reaction with diphenyl carbonate, also shown in Table 1.

The chemical species in the product mixture were quantified using a Gas Chromatography method, where standards of each the different species were used to obtain the calibration curves. The results are shown in Table 1.

TABLE 1

| Example | 1 | 2 | 3 | 4 | 5 | 6 | 7 | 8 | 9 | 10 | 11 |
|---|---|---|---|---|---|---|---|---|---|---|---|
| Reaction Time (min) | 120 | 120 | 120 | 120 | 5 | 5 | 10 | 10 | 120 | 120 | 120 |
| Reaction Temperature (° C.) | 150 | 150 | 150 | 150 | 150 | 170 | 150 | 170 | 150 | 150 | 30 |
| MeOH content in Acetone (ppm) | 495 | 495 | 479 | 495 | 495 | 495 | 495 | 495 | 495 | 495 | 495 |
| DPC content in reaction mixture (ppm) | 32,339 | 3,199 | 32,030 | 34,954 | 32,339 | 32,339 | 32,339 | 32,339 | 32,030 | 3,210 | 32,030 |
| Catalyst concentration in water (wt %) | 15 | 0.15 | 0.15 | 15 | 15 | 15 | 15 | 15 | 15 | 15 | 15 |
| mmol catalyst per mol MeOH | 10 | 1 | 10 | 0 | 10 | 10 | 10 | 10 | 1 | 10 | 10 |
| Reaction Products (ppm) | | | | | | | | | | | |
| Methanol | 0 | 225 | 63 | 385 | 58 | 50 | 40 | 27 | 287 | 138 | 270 |
| MIBK | 0 | 0 | 0 | 0 | 0 | 0 | 0 | 0 | 0 | 0 | 0 |
| Anisole | 34 | 2 | 17 | 0 | 9 | 25 | 0 | 15 | 0 | 10 | 0 |
| Phenol | 7,859 | 518 | 19,230 | 0 | 7,846 | 9,020 | 6,632 | 7,230 | 468 | 2,440 | 490 |
| O-Cresol | 0 | 0 | 0 | 0 | 0 | 0 | 0 | 0 | 0 | 0 | 0 |
| PMC | 2,486 | 528 | 2,133 | 0 | 3,748 | 4,057 | 2,332 | 2,171 | 392 | 372 | 190 |
| DPC | 21,742 | 2,094 | 9,518 | 34,954 | 25,290 | 23,981 | 28,233 | 26,127 | 20,988 | 15 | 22,373 |
| Methanol removal | 100% | 55% | 87% | 22% | 88% | 90% | 92% | 95% | 42% | 72% | 45% |

Examples 1-11 of Table 1 illustrate that the amount of methanol is significantly reduced when 10 mmol of TMAOH/mol methanol is added versus 1 mmol of TMAOH/mol methanol. For example, Examples 1, 3, 5, and 6-8 all had a molar ratio of 10 mmol of TMAOH/mol methanol and results in 87-100 wt % of the methanol being removed. The examples illustrate that the ratio of diphenylcarbonate to methanol should be greater than stoichiometric to help to reduce the degradation reactions that can occur of diphenyl carbonate. Table 1 also illustrates in Examples 5 and 6, that the reaction between methanol and DPC is quick by achieving high conversions even at only 5 minutes of reaction time. Examples 1 and 3 further illustrate that the amount of water in the catalyst can have an effect on the hydrolysis of DPC. Specifically, Examples 1 and 3 show that there is a larger disappearance of DPC when catalyst is more diluted in water. Example 11 illustrates that a reaction temperature of only 30° C. resulted in a significant reduction in the methanol removal as compared to reactions at 150° C.

Examples 12-14: Effect of Methanol in Recovered Diphenyl Carbonate

Acetone was recovered from a mixture comprising acetone and diphenyl carbonate. The methanol content in the recovered acetone was determined and is shown in Table 2. The recovered acetone was then reacted with phenol in a continuous lab-scale reaction of bisphenol A by feeding 5 wt % of the recovered acetone in phenol to a reactor containing 50 grams (g) of dry, fresh catalyst. The catalyst was a 2 wt % cross-linked sulfonated polystyrene resin with a cysteamine copromoter at a loading 20 mole percent (mol %) based on the available acid groups. The drop in acetone conversion after three months was determined and is shown in Table 2.

TABLE 2

| Example | 12 | 13 | 14 |
|---|---|---|---|
| Methanol content in recovered acetone (ppm) | 5000 | 250 | <20 |
| Drop in conversion of acetone (%) | 20 | 5 | 1 |

Table 2 shows that the drop in conversion of acetone is significantly reduced as the methanol content in the recovered acetone is reduced and that a drop in conversion of 1% is attained at a methanol content of less than 20 ppm.

Examples 15-16: Effect of Ketone in Diphenyl Carbonate

Acetone contaminated with 1 wt % methyl isobutyl ketone was used reacted with phenol to produce bisphenol A and compared to a bisphenol A prepared from acetone that is free of methyl isobutyl ketone. Specifically, a reactor feed comprising 4 wt % acetone, 11 wt % para-para-BPA, 2.8 wt % ortho-para-BPA, 0.2 wt % water, and 6 wt % of other byproducts was added to a reactor comprising a catalyst. The catalyst was a 2 wt % cross-linked sulfonated polystyrene resin with a cysteamine copromoter at a loading 20 mol % based on the available acid groups. After the reaction, the effluent was treated in an adduct crystallization process, the isolated adduct was washed with phenol and the phenol was removed in a vacuum distillation process. The purity of the bisphenol A produced and the APHA color is shown in Table 3 and is compared to a bisphenol A with a methyl isobutyl ketone content of less than 100 ppm. The results are shown in Table 3.

The bisphenol A of Examples 15 and 16 was then used in a melt polymerization and the resultant yellowness was determined. The results are shown in Table 3.

TABLE 3

| Example | 15 | 16 |
|---|---|---|
| Methyl isobutyl ketone in acetone | <100 ppm | 1 wt % |
| Bisphenol product | | |
| Bisphenol purity (wt %) | 99.6-99.7 | 99.2-99.3 |
| APHA color | 5-7 | 20-50 |
| Polycarbonate | | |
| Polycarbonate yellowness | 1.5-2 | 2-3 |

Table 3 shows that methyl isobutyl ketone in acetone results in a reduced bisphenol A purity of only 99.2-99.3 wt % as compared to a bisphenol A purity of 99.6-99.7 wt % and an increased APHA color of 20-50 as compared to an APHA color of only 5-7.

Examples 17-23: Effect of Metal in Diphenyl Carbonate

Similar to Examples 12-14, polycarbonate was polymerized from bisphenol A derived from recovered acetone to, except that the acetone comprised 1 ppm iron instead of the methanol. The polycarbonate with such a high iron content resulted in a polycarbonate that was not transparent and that had an APHA color of greater than 20. Such a polycarbonate could not be used for transparent applications, for example, for use as a compact disc.

TABLE 4

| Example | Fe in PC (ppm) | APHA Color |
|---|---|---|
| 17 | 0.15 | 10.7 |
| 18 | 0.32 | 18.0 |
| 19 | 0.56 | 23.1 |
| 20 | 0.71 | 32.3 |
| 21 | 0.54 | 26.4 |
| 22 | 0.50 | 21.4 |
| 23 | 0.73 | 30.6 |

Set forth below are some embodiments of the present method of polymerizing a polycarbonate.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

Set forth below are some embodiments of the methods, polycarbonate, and use of the acetone monomer mixture disclosed herein.

Embodiment 1

A method for producing an aryl alkyl carbonate, comprising: reacting a methanol with a diaryl carbonate in the presence of a catalyst to form a mixture comprising the aryl alkyl carbonate and a hydroxy compound, wherein the methanol is in an acetone monomer mixture comprising an acetone and at least one of the diaryl carbonate and the dihydroxy compound; and separating the aryl alkyl carbonate from the mixture. The reacting can optionally be at one or more of a temperature of greater than or equal to 50° C., a ratio of mmol of TMAOH/mol methanol of greater than or equal to 2, and a catalyst concentration in water can be greater than 0.1 wt %.

Embodiment 2

A method for forming a dihydroxy compound comprising: reacting a methanol with a diaryl carbonate in the presence of a catalyst to form a mixture comprising an aryl alkyl carbonate and a hydroxy compound, wherein the methanol is in an acetone monomer mixture comprising an acetone and at least one of the diaryl carbonate and the dihydroxy compound; separating the aryl alkyl carbonate from the mixture; optionally separating out one or more byproducts from the mixture; and reacting the acetone in the mixture with a second hydroxy compound to produce the dihydroxy compound.

Embodiment 3

The method of Embodiment 2, wherein the hydroxy compound and the second hydroxy compound are the same material.

Embodiment 4

The method of Embodiment 2, wherein the hydroxy compound and the second hydroxy compound are phenol; and wherein the dihydroxy compound is bisphenol A.

Embodiment 5

A method for producing a polycarbonate by melt polymerization, comprising: adding an acetone, a diaryl carbonate, and a dihydroxy compound to a melt polymerization unit, wherein the acetone is added as an acetone monomer mixture to the melt polymerization unit with the a monomer comprising the diaryl carbonate and/or the dihydroxy compound; melt polymerizing the dihydroxy compound and the diaryl carbonate to produce the polycarbonate; recovering a recovered acetone from the melt polymerization unit; adding the recovered acetone to a reaction vessel, wherein the recovered acetone in the reaction vessel has one or more of a methanol content of less than or equal to 100 ppm, and a ketone and aldehyde content of less than or equal to 100 ppm; reacting the recovered acetone to produce a second dihydroxy compound; and adding the second dihydroxy compound to the melt polymerization unit.

Embodiment 6

A method for producing a polycarbonate by melt polymerization, comprising: separating an acetone from an acetone monomer mixture to form a separated acetone and a separated monomer; adding the separated monomer and a second monomer to a melt polymerization unit, wherein the separated monomer comprises a dihydroxy compound and the second monomer comprises a diaryl carbonate or the separated monomer comprises the diaryl carbonate and the second monomer comprises the dihydroxy compound; melt polymerizing the dihydroxy compound and the diaryl carbonate to produce the polycarbonate; adding the separated acetone to a reaction vessel, wherein the separated acetone in the reaction vessel has one or more of a methanol content of less than or equal to 100 ppm, and a ketone and aldehyde content of less than or equal to 100 ppm; reacting the separated acetone with a monohydroxy compound to produce a second dihydroxy compound; and adding the second dihydroxy compound to the melt polymerization unit.

Embodiment 7

An integrated method for producing a polycarbonate, comprising: making an acetone monomer mixture comprising a monomer and an acetone, wherein the acetone and/or the monomer has one or more of a methanol content of less than or equal to 100 ppm, and a ketone and aldehyde content of less than or equal to 100 ppm; transporting the acetone monomer mixture to a polycarbonate production plant; reacting the monomer and a second monomer in a melt polymerization unit to produce the polycarbonate, wherein the monomer comprises a dihydroxy compound and the second monomer comprises a diaryl carbonate or the monomer comprises the diaryl carbonate and the second monomer comprises the dihydroxy compound; separating a separated acetone from the acetone monomer mixture prior to the reacting and/or recovering a recovered acetone during the reacting; adding the separated acetone and/or the recovered acetone to a reaction vessel; reacting the separated acetone and/or the recovered acetone to produce a second dihydroxy compound; and adding the second dihydroxy compound to the melt polymerization unit.

Embodiment 8

The method of Embodiment 7, wherein a temperature during transporting is 20 to 70° C.

Embodiment 9

The method of any of Embodiments 5-8, wherein the second dihydroxy compound comprises less than or equal to 38 ppb molybdenum; less than or equal to 38 ppb vanadium; less than or equal to 38 ppb chromium; less than or equal to 85 ppb titanium; less than or equal to 425 ppb niobium; less than or equal to 38 ppb nickel; less than or equal to 12 ppb zirconium; less than or equal to 12 ppb iron, or a combination comprising one or more of the foregoing based on the total weight of the second dihydroxy compound.

Embodiment 10

The method of any of Embodiments 5-9, further comprising forming the diaryl carbonate.

Embodiment 11

The method of any of Embodiments 5-10, further comprising removing a methanol from the acetone by reacting the methanol with a removal diaryl carbonate in the presence of a removal catalyst to form an aryl alkyl carbonate and a hydroxy compound; and separating the aryl alkyl carbonate and the hydroxy compound from the acetone; wherein the removal diaryl carbonate optionally comprises diphenyl carbonate.

Embodiment 12

The method of any of Embodiments 1-4 and 11, wherein the diaryl carbonate comprises diphenyl carbonate, the aryl alkyl carbonate comprises phenyl methyl carbonate, and the hydroxy compound comprises phenol.

Embodiment 13

The method of any of the preceding Embodiments, wherein a molar ratio of the acetone to monomer in the acetone monomer mixture is 0.5:1 to 7:1.

Embodiment 14

The method of any of the preceding Embodiments, wherein the acetone monomer mixture comprises diaryl carbonate.

Embodiment 15

The method of any of the preceding Embodiments, wherein the diaryl carbonate has the formula (I)

(I)

wherein n is an integer 1 to 3 and each $R_2$ is independently, a $C_{1-34}$ alkyl, a $C_{1-34}$ alkoxy, a $C_{5-34}$ cycloalkyl, a $C_{7-34}$ alkylaryl; a $C_{6-34}$ aryl; a halogen radical, or —COO—R', wherein R' is H, a $C_{1-34}$ alkyl, a $C_{1-34}$ alkoxy, a $C_{5-34}$ cycloalkyl, a $C_{7-34}$ alkylaryl; or a $C_{6-34}$ aryl.

Embodiment 16

The method of any of the preceding Embodiments, wherein the diaryl carbonate comprises diphenyl carbonate and wherein the dihydroxy compound comprises bisphenol A.

Embodiment 17

A polycarbonate formed by the method of any of Embodiments 5-16.

Embodiment 18

The polycarbonate of Embodiment 17, wherein the polycarbonate has a metal level of less than or equal to 38 ppb of molybdenum; less than or equal to 38 ppb of vanadium; less than or equal to 38 ppb of chromium; less than or equal to 85 ppb of titanium; less than or equal to 425 ppb of niobium; less than or equal to 38 ppb of nickel; less than or equal to 12 ppb of zirconium; less than or equal to 12 ppb of iron, or a combination comprising one or more of the foregoing.

Embodiment 19

The use of an acetone monomer mixture in the production of bisphenol A, wherein the acetone monomer mixture comprising an acetone and at least one of a diaryl carbonate and a dihydroxy compound, and wherein the acetone monomer mixture comprises less than or equal to 100 ppm of an alcohol, less than or equal to 100 ppm of an aldehyde, and less than or equal to 100 ppm of a ketone other than acetone, based on the total weight of the acetone.

Embodiment 20

The use of an acetone monomer mixture in the production of bisphenol A, wherein the acetone monomer mixture comprising an acetone and at least one of a diaryl carbonate and a dihydroxy compound, and wherein the acetone monomer mixture comprises less than or equal to 100 ppm of a methanol, based on the total weight of the acetone.

Embodiment 21

The use of an acetone monomer mixture in the production of bisphenol A, wherein the acetone monomer mixture comprising an acetone and at least one of a diaryl carbonate and a dihydroxy compound, and wherein a methanol in the acetone monomer mixture has been reacted with a removal diaryl carbonate in the presence of a removal catalyst to form an aryl alkyl carbonate, and wherein the aryl alkyl carbonate has been removed before production the bisphenol A.

All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The modifier "about" used in connection with a quantity is inclusive of the stated value and has the meaning dictated by the context (e.g., includes the degree of error associated with measurement of the particular quantity). "Or" means "and/or."

With respect to the figures, it is noted that these figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the description for the sake of clarity, these terms are intended to refer only to the particular structure of the embodiments selected for illustration in the drawings, and are not intended to define or limit the scope of the disclosure. In the drawings and the description herein, it is to be understood that like numeric designations refer to components of like function.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

Disclosure of a narrower range in addition to a broader range is not a disclaimer of the broader range. Unless defined otherwise, technical and scientific terms used herein have the same meaning as is commonly understood by one of skill in the art to which this invention belongs. "Optional" or "optionally" means that the subsequently described event or circumstance can or cannot occur, and that the description includes instances where the event occurs and instances where it does not.

While particular embodiments have been described, alternatives, modifications, variations, improvements, and substantial equivalents that are or may be presently unforeseen may arise to Applicants or others skilled in the art. Accordingly, the appended claims as filed and as they may be amended are intended to embrace all such alternatives, modifications variations, improvements, and substantial equivalents.

This application claims priority to European Patent Application 14382331 filed on 5 Sep. 2014, the contents of which are incorporated in their entirety by reference.

We claim:

1. A method for removing methanol present in an acetone monomer mixture, comprising:
    reacting the methanol with a diaryl carbonate in the presence of a catalyst to form an aryl alkyl carbonate and a hydroxy compound, wherein the acetone monomer mixture comprises acetone and at least one of the diaryl carbonate and a dihydroxy compound; and separating the aryl alkyl carbonate.

2. The method of claim 1, further comprising:

reacting the acetone with a second hydroxy compound to produce the dihydroxy compound.

3. The method of claim 2, wherein the hydroxy compound and the second hydroxy compound are the same material.

4. The method of claim 2, wherein the hydroxy compound and the second hydroxy compound are phenol; and wherein the dihydroxy compound is bisphenol A.

5. A method for producing a polycarbonate by melt polymerization, comprising:

adding an acetone, a diaryl carbonate, and a dihydroxy compound to a melt polymerization unit, wherein the acetone is added as an acetone monomer mixture to the melt polymerization unit with the a monomer comprising the diaryl carbonate and/or the dihydroxy compound;

melt polymerizing the dihydroxy compound and the diaryl carbonate to produce the polycarbonate;

recovering a recovered acetone from the melt polymerization unit;

adding the recovered acetone to a reaction vessel, wherein the recovered acetone in the reaction vessel has one or more of a methanol content of less than or equal to 100 ppm, and a ketone and aldehyde content of less than or equal to 100 ppm both based on a total weight of the recovered acetone;

reacting the recovered acetone to produce a second dihydroxy compound; and adding the second dihydroxy compound to the melt polymerization unit.

6. A method for producing a polycarbonate by melt polymerization, comprising:

separating an acetone from an acetone monomer mixture to form a separated acetone and a separated monomer;

adding the separated monomer and a second monomer to a melt polymerization unit, wherein the separated monomer comprises a dihydroxy compound and the second monomer comprises a diaryl carbonate or the separated monomer comprises the diaryl carbonate and the second monomer comprises the dihydroxy compound;

melt polymerizing the dihydroxy compound and the diaryl carbonate to produce the polycarbonate;

adding the separated acetone to a reaction vessel, wherein the separated acetone in the reaction vessel has one or more of a methanol content of less than or equal to 100 ppm, and a ketone and aldehyde content of less than or equal to 100 ppm both based on a total weight of the separated acetone;

reacting the separated acetone with a monohydroxy compound to produce a second dihydroxy compound; and adding the second dihydroxy compound to the melt polymerization unit.

7. The method of claim 6, further comprising:

prior to the separating the acetone, making the acetone monomer mixture comprising the separated monomer and an acetone, wherein the acetone and/or the separated monomer has one or more of a methanol content of less than or equal to 100 ppm, and a ketone and aldehyde content of less than or equal to 100 ppm;

prior to the melt polymerizing, transporting the acetone monomer mixture to a polycarbonate production plant; and optionally recovering a recovered acetone during the melt polymerizing;

adding the separated acetone and/or the recovered acetone to a reaction vessel;

reacting the separated acetone and/or the recovered acetone to produce a second dihydroxy compound; and adding the second dihydroxy compound to the melt polymerization unit.

8. The method of claim 7, wherein a temperature during transporting is 20 to 70° C.

9. The method of claim 5, wherein the second dihydroxy compound comprises less than or equal to 38 ppb molybdenum; less than or equal to 38 ppb vanadium; less than or equal to 38 ppb chromium; less than or equal to 85 ppb titanium; less than or equal to 425 ppb niobium; less than or equal to 38 ppb nickel; less than or equal to 12 ppb zirconium; less than or equal to 12 ppb iron, or a combination comprising one or more of the foregoing based on the total weight of the second dihydroxy compound.

10. The method of claim 5, further comprising forming the diaryl carbonate.

11. The method of claim 5, further comprising removing a methanol from the acetone monomer mixture and/or from the separated acetone by reacting the methanol with a removal diaryl carbonate in the presence of a removal catalyst to form an aryl alkyl carbonate and a hydroxy compound; and separating the aryl alkyl carbonate and the hydroxy compound from the acetone; wherein the removal diaryl carbonate optionally comprises diphenyl carbonate.

12. The method of claim 1, wherein the diaryl carbonate comprises diphenyl carbonate, the aryl alkyl carbonate comprises phenyl methyl carbonate, and the hydroxy compound comprises phenol.

13. The method of claim 1, wherein a molar ratio of the acetone to the monomer in the acetone monomer mixture is 0.5:1 to 7:1.

14. The method of claim 1, wherein the acetone monomer mixture comprises diaryl carbonate.

15. The method of claim 1, wherein the diaryl carbonate has the formula (I)

wherein n is an integer 1 to 3 and each $R_2$ is independently, a $C_{1-34}$ alkyl, a $C_{1-34}$ alkoxy, a $C_{5-34}$ cycloalkyl, a $C_{7-34}$ alkylaryl; a $C_{6-34}$ aryl; a halogen radical, or —COO—R', wherein R' is H, a $C_{1-34}$ alkyl, a $C_{1-34}$ alkoxy, a $C_{5-34}$ cycloalkyl, a $C_{7-34}$ alkylaryl; or a $C_{6-34}$ aryl.

16. The method of claim 1, wherein the diaryl carbonate comprises diphenyl carbonate and wherein the dihydroxy compound comprises bisphenol A.

17. A polycarbonate formed by the method of claim 5, wherein the polycarbonate has a metal level of less than or equal to 38 ppb of molybdenum; less than or equal to 38 ppb of vanadium; less than or equal to 38 ppb of chromium; less than or equal to 85 ppb of titanium; less than or equal to 425 ppb of niobium; less than or equal to 38 ppb of nickel; less than or equal to 12 ppb of zirconium; less than or equal to 12 ppb of iron, or a combination comprising one or more of the foregoing based on a total weight of the polycarbonate.

18. The method of claim 1, wherein the mixture comprises one or both of a methanol content of less than or equal to 100 ppm, and a ketone and aldehyde content of less than or equal to 100 ppm based on a total weight of the acetone.

19. The method of claim 7, further comprising removing a methanol from the acetone before or after making the acetone monomer mixture by reacting the methanol with a removal diaryl carbonate in the presence of a removal catalyst to form an aryl alkyl carbonate and a hydroxy compound; and separating the aryl alkyl carbonate and the hydroxy compound from the acetone.

20. The method of claim 6, wherein a molar ratio of the acetone to the monomer in the acetone monomer mixture is 0.5:1 to 7:1.

* * * * *